Aug. 21, 1973 M. B. WAKEFIELD Plant Pat. 3,386
DOGWOOD TREE
Filed Jan. 4, 1972
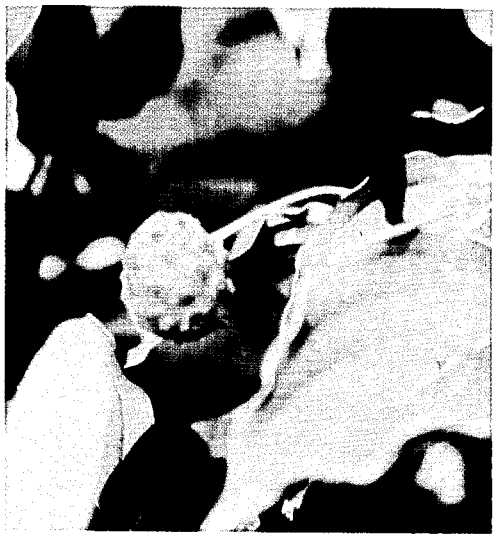
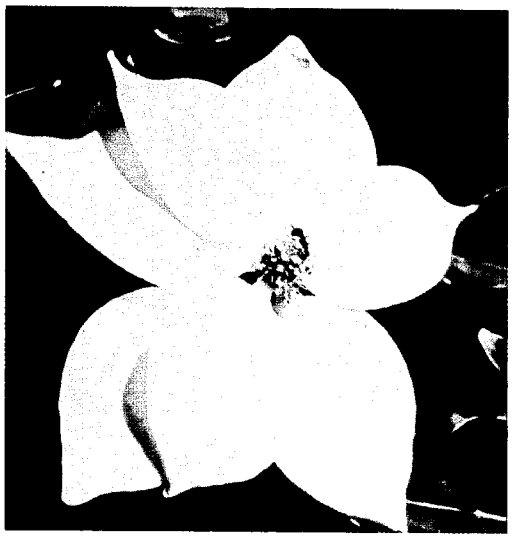
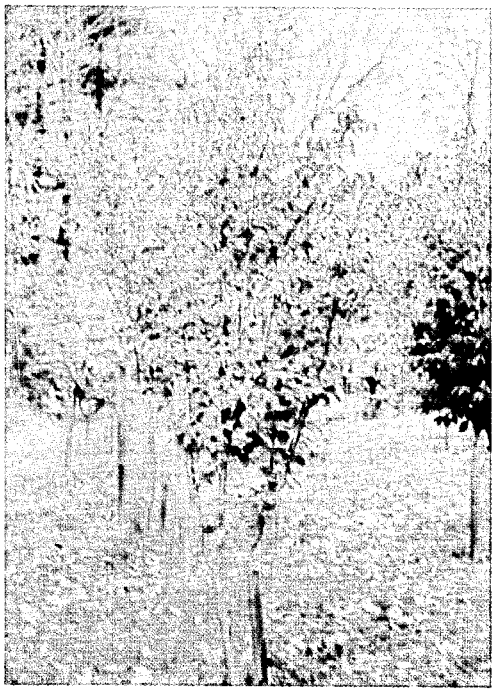
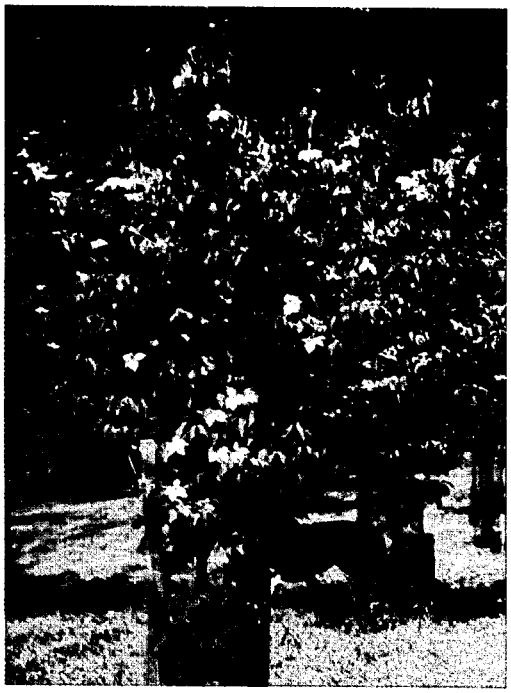

United States Patent Office

Plant Pat. 3,386
Patented Aug. 21, 1973

3,386
DOGWOOD TREE

Mary B. Wakefield, 1465 Brush Hill Road,
Milton, Mass. 02186

Filed Jan. 4, 1972, Ser. No. 215,441
Int. Cl. A01h 5/12
U.S. Cl. Plt.—51 1 Claim The present invention relates to a new and distinct variety of dogwood tree of the Japanese dogwood type botanically known as *Cornus kousa,* which was originated by me from a seed that was planted by me in my nursery located at Milton, Mass.

When I acquired this seed, I was attending classes on plant propagation, as conducted at the Arnold Arboretum which is near my home in Milton, Mass. My interest in plant propagation and experimentation led me to seek and receive permission to obtain seeds of various plants, including dogwoods, being grown at the Arnold Arboretum. This particular dogwood seed was taken by me from a large-fruited dogwood tree specimen of the kousa type which had attracted my attention at the Arboretum and which I understood was of uncertain origin and parentage. In a few years after planting a number of seeds which I had taken from this Arboretum specimen, my attention was attracted to one particular seedling among the block I was growing in my nursery aforementioned, due to the fact that its inflorescences had more than the normal number of four bracts that have usually been characteristic of this dogwood species. Accordingly, I carefully preserved the noted seedling, and in due course, I propagated it by rooted cuttings taken therefrom.

After continuously observing and testing the original seedling and its progeny produced therefrom by the rooted cuttings referred to in the foregoing, I found that the bract count consistently varied from 6 to 9 per flower (inflorescence), thereby giving the distinctive effect of a double flower form. This feature, combined with other distinctive characteristics later noted in my observations and tests, has convinced me that my new seedling represents a unique, improved, and commercially available dogwood variety which is distinguished from its parent, as well as from all other dogwood varieties of which I am aware, as particularly evidenced by the following characteristics which are outstanding therein:

(1) An upright and compact habit of growth which requires very little, if any, pruning or maintenance;

(2) Attractive dark green neat foliage which turns in color to wine red in the fall (usually in the month of November in Milton, Mass.);

(3) Attractive white flowers of medium size and having a greater bract count, varying from 6 to 9 bracts per flower, than is normal for the species;

(4) Large edible fruit which turn from green to yellow to clear bright red in color and which particularly tend to attract birds;

(5) A distinctive golden brown winter color of the smooth bark of the twigs and young branches which are quite ornamental; and (6) Especial suitability for street, park and garden plantings.

The accompanying drawings show a typical tree specimen of my new dogwood variety as it appears during the blooming season; an individual typical bloom as shown on a somewhat larger scale; a typical fruit specimen in its red color stage; and a young tree specimen with its foliage in the red fall color stage.

The following is a detailed description of my new dogwood variety, with color terminology in accordance with the Royal Horticultural Colour Chart, published by the Royal Horticultural Society of London, except where general color terms of ordinary dictionary significance are obvious:

Breeding: A seedling grown from seed derived from an unnamed and unpatented variety of the species *C. kousa* of uncertain origin and parentage.

Propagation: Holds its distinguishing characteristics through succeeding propagations by rooted cuttings.

Locality where grown and observed: Milton, Mass.

Tree: Small; upright; dense; hardy (has withstood temperatures as low as −20° F. without injury during winters in Massachusetts.

*Trunk.*—Slender; smooth. Bark color—Brown.

*Branches.*—Slender; smooth. Bark color—Brown.

*Twigs and young branchlets.*—Smooth; ornamental. Bark color—distinctive golden brown in winter season.

Leaf buds: Color—greyed red 182, with pubescence paler than greyed green 189 D.

Foliage: Neat; abundant.

*Leaves.*—Length—about 3⅜ inches. Width—from about 1½ inches to 1⅝ inches. Shape—acuminate. Color—dark green blend of colors 133A and 136A; turn wine red in fall season (usually in November in Massachusetts). Margin—serrate, with pale green edge. Petiole—medium length.

Flower buds: Hardy; have withstood winter temperatures as low as −20° F. in Massachusetts without injury.

*Size.*—Length—about 4/16 inch. Width—about 5/32 inch. Shape—ovoid; sessile and abruptly short acuminate. Color—greyed red 182, with pubescence paler than greyed green 189 D.

Flowers (inflorescence):

*Dates of first and full bloom.*—About June 1 and June 15, respectively in Milton, Mass.

*Quantity.*—Normal, becoming more abundant as tree ages.

*Size.*—Medium.

*Petalage (bracts).*—Number of bracts—from 6 to 9. Shape—from elliptic to ovate. Size—Length—average about 2¾ inches. Width—average about 1⅞ inches. Color—creamy white when first opening but gradually turning pure white as flowers open and mature.

*Lasting quality.*—Longer lasting than normal for the 4-bracted species.

Fruit:

*Size.*—Large; about 1 inch in diameter.

*Color.*—Changes from green to yellow to clear bright red; especially attractive to birds.

General observations: The most striking feature of my new variety is its long lasting and attractive white flowers of more double form than is normal for the species.

I claim:

1. A new and distinct variety of dogwood tree of the Japanese dogwood type, substantially as herein shown and described, characterized particularly as to novelty by the unique combination of an upright and compact habit of growth which requires very little, if any, pruning or maintenance, attractive dark green neat foliage which turns in color to wine red in the fall (usually in the month of November in Milton, Mass.), attractive white flowers of medium size and having a greater bract count, varying from 6 to 9 bracts per flower, than is normal for the species, large edible fruit which turn from green to yellow to clear bright red in color and which particularly tend to attract birds, a distinctive golden brown winter color of the smooth bark of the twigs and young branchlets which are quite ornamental, and especial suitability for street, park and garden plantings.

No references cited.

ROBERT E. BAGWILL, Primary Examiner